US011521166B2

(12) United States Patent
Scriber et al.

(10) Patent No.: US 11,521,166 B2
(45) Date of Patent: Dec. 6, 2022

(54) SYSTEMS AND METHODS FOR SECURE FULFILLMENT TRACKING USING A SHARED REGISTRY

(71) Applicant: CABLE TELEVISION LABORATORIES, INC, Louisville, CO (US)

(72) Inventors: Brian Alexander Scriber, Denver, CO (US); Michael Glenn, Golden, CO (US); Steven J. Goeringer, Westminster, CO (US)

(73) Assignee: Cable Television Laboratories, Inc., Louisville, CO (US)

( * ) Notice: Subject to any disclaimer, the term of this patent is extended or adjusted under 35 U.S.C. 154(b) by 131 days.

(21) Appl. No.: 16/141,757

(22) Filed: Sep. 25, 2018

(65) Prior Publication Data

US 2019/0096522 A1 Mar. 28, 2019

Related U.S. Application Data

(60) Provisional application No. 62/562,722, filed on Sep. 25, 2017.

(51) Int. Cl.
*G06Q 10/08* (2012.01)
*H04L 9/30* (2006.01)
(Continued)

(52) U.S. Cl.
CPC ....... *G06Q 10/087* (2013.01); *G06Q 30/0633* (2013.01); *H04L 9/30* (2013.01);
(Continued)

(58) Field of Classification Search
None
See application file for complete search history.

(56) References Cited

U.S. PATENT DOCUMENTS 5,892,900 A * 4/1999 Ginter .................... G06Q 20/12
726/26
2015/0332283 A1* 11/2015 Witchey ............... G06Q 30/018
705/3
(Continued)

OTHER PUBLICATIONS

Anonymous, Universal Blockchained Health Record, IP.com (Year: 2016).*
(Continued)

*Primary Examiner* — Jacob C. Coppola
*Assistant Examiner* — Eduardo Castilho
(74) *Attorney, Agent, or Firm* — Armstrong Teasdale LLP

(57) ABSTRACT

An ecosystem for monitoring the status of a consumable good is provided. The ecosystem includes an identification registry configured to (i) store identifying information regarding a consumer, and (ii) associate the stored identifying information with a unique cryptographic consumer identifier. The ecosystem further includes a transaction registry configured to (i) receive a fulfillment order for a consumable good, and (ii) generate a unique cryptographic transaction identifier for fulfillment of the fulfillment order. The ecosystem further includes a fulfillment computer subsystem configured to (i) receive the fulfillment order, (ii) verify the consumer identifier, and (iii) validate the transaction identifier. The ecosystem further includes a distributed ledger configured to encode transaction details relating to the fulfillment order.

20 Claims, 3 Drawing Sheets

(51) Int. Cl.
*H04L 9/32* (2006.01)
*G06Q 30/06* (2012.01)
*H04L 9/00* (2022.01)
*G16H 20/10* (2018.01)

(52) U.S. Cl.
CPC .......... *H04L 9/3239* (2013.01); *H04L 9/3247* (2013.01); *H04L 9/3268* (2013.01); *G06Q 2220/00* (2013.01); *G16H 20/10* (2018.01); *H04L 9/50* (2022.05); *H04L 2209/88* (2013.01)

(56) References Cited

U.S. PATENT DOCUMENTS

| | | | | |
|---|---|---|---|---|
| 2016/0098730 | A1* | 4/2016 | Feeney | G06Q 20/3825 705/71 |
| 2016/0117471 | A1* | 4/2016 | Belt | G06F 19/3456 705/2 |
| 2016/0300234 | A1* | 10/2016 | Moss-Pultz | G06Q 20/3827 |
| 2016/0350728 | A1* | 12/2016 | Melika | G06Q 20/02 |
| 2017/0132393 | A1* | 5/2017 | Natarajan | G06Q 10/087 |
| 2017/0140145 | A1* | 5/2017 | Shah | G16H 80/00 |
| 2017/0149560 | A1* | 5/2017 | Shah | G06Q 50/24 |
| 2017/0300627 | A1* | 10/2017 | Giordano | G06F 21/645 |
| 2018/0075028 | A1* | 3/2018 | Ruschin | G06F 16/93 |
| 2018/0082290 | A1* | 3/2018 | Allen | G06Q 20/367 |
| 2018/0096175 | A1* | 4/2018 | Schmeling | G06Q 10/00 |
| 2018/0121620 | A1* | 5/2018 | Bastide | G16H 20/10 |
| 2018/0139043 | A1* | 5/2018 | Jayachandran | G06Q 20/065 |
| 2018/0322491 | A1* | 11/2018 | Madisetti | G06Q 20/3823 |
| 2019/0074077 | A1* | 3/2019 | Kuo | G16H 10/60 |
| 2019/0198144 | A1* | 6/2019 | Blackley | G06F 16/27 |
| 2019/0206536 | A1* | 7/2019 | Hausman | H04L 9/3226 |
| 2019/0237176 | A1* | 8/2019 | O'brien | G06Q 20/065 |
| 2019/0362828 | A1* | 11/2019 | Laxer | G06Q 10/087 |

OTHER PUBLICATIONS

Anonymous, Blockchain/Cognitive Technology Platform as an Adviser to Support Pharmacy Operations: Drug Use Management and Drug Inventory Management, IP.com (Year: 2017).*

X. Xu et al., "The Blockchain as a Software Connector," 2016 13th Working IEEE/IFIP Conference on Software Architecture (WICSA), 2016, pp. 182-191, doi: 10.1109/WICSA.2016.21. (Year: 2016).*

Wu, H.; Li, Z.; King, B.; Ben Miled, Z.; Wassick, J.; Tazelaar, J. A Distributed Ledger for Supply Chain Physical Distribution Visibility. Information 2017, 8, 137. https://doi.org/10.3390/info8040137 (Year: 2017).*

Schöner, Manuela M., et al. "Blockchain technology in the pharmaceutical industry." Frankfurt School Blockchain Center: Frankfurt, Germany (2017). (Year: 2017).*

Firouzi Jahantigh, Farzad & Malmir, Behnam. (2015). Development of a supply chain model for healthcare industry. IEOM 2015—5th International Conference on Industrial Engineering and Operations Management, Proceeding. 10.1109/IEOM.2015.7093935. (Year: 2015).*

* cited by examiner

SYSTEMS AND METHODS FOR SECURE FULFILLMENT TRACKING USING A SHARED REGISTRY

FIELD

The field of the disclosure relates generally to tracking of materials and data, and more particularly, to tracking consumable materials requiring medical prescriptions using distributed ledger technology.

BACKGROUND

Loss, misuse, and theft of materials and data is a critical problem in many industries. Furthermore, the details of how such material and data are used, and by which people, are important to know. This problem is more pronounced when the material and/or data are "consumable goods," that is, materials or data products that are capable of being consumed, destroyed, dissipated, wasted, or spent. In one particular example, in the field of pharmaceutical materials, it may be very important, for insurance and safety reasons, to have information pertaining to the details of how opioids traverse a medical environment. Particular individuals may have a significant incentive to falsify records of how such materials, as well as associated data, are used in order to, for example, hide evidence of theft or other crimes, and/or acts of negligence or malpractice. Conventional methods, which rely on manual processes augmented by traditional databases, do not provide sufficient security transparency and visibility to attest confidently the disposition of critical materials as they traverse a system.

Consumable goods such as pharmaceutical prescriptions are at particular risk of fraud, misuse, reuse, and error. Over-prescription and/or prescription theft of high-value pharmaceutical drugs may occur when a prescription-seeker has a pharmaceutical prescription filled at a first pharmacy or distribution location, and then has the same prescription filled again at another location. Improper opioid acquisition, for example, is commonly performed in this way. Conventional databases and reporting systems have not been able to reliably prevent such abuse. Furthermore, where prevention mechanisms have been attempted, legitimate consumers/patients have found such mechanisms to be invasive and/or difficult to manage (e.g., pseudoephedrine acquisition), and the patient data entered into such protection systems is not always secure from access to illegitimate third parties.

Accordingly, it is desirable to create a more secure system to track the prescription and distribution of consumable goods such as narcotics and other controlled substances, while also increasing the security of patient records.

BRIEF SUMMARY

In an aspect, an ecosystem for monitoring the status of a consumable good is provided. The ecosystem includes an identification registry configured to (i) store identifying information regarding a consumer, and (ii) associate the stored identifying information with a unique cryptographic consumer identifier. The ecosystem further includes a transaction registry configured to (i) receive a fulfillment order for a consumable good, and (ii) generate a unique cryptographic transaction identifier for fulfillment of the fulfillment order. The ecosystem further includes a fulfillment computer subsystem configured to (i) receive the fulfillment order, (ii) verify the consumer identifier, and (iii) validate the transaction identifier. The ecosystem further includes a distributed ledger configured to encode transaction details relating to the fulfillment order.

BRIEF DESCRIPTION OF THE DRAWINGS

These and other features, aspects, and advantages of the present disclosure will become better understood when the following detailed description is read with reference to the following accompanying drawings, in which like characters represent like parts throughout the drawings.

Figure 1:
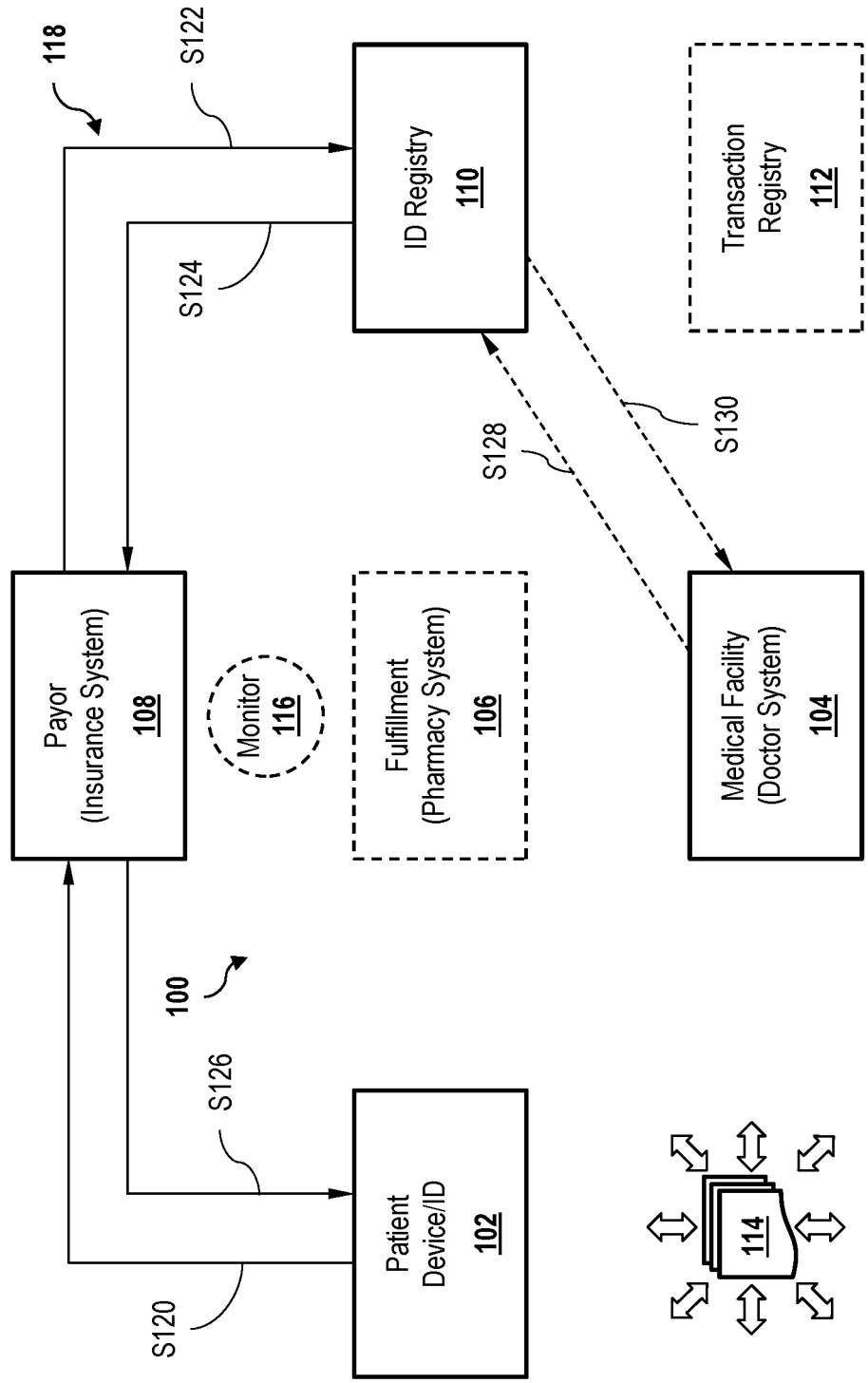
FIG. 1 is a schematic illustration of an ecosystem for fulfillment of a consumable good order by a consumer, according to an embodiment.

Unless otherwise indicated, the drawings provided herein are meant to illustrate features of embodiments of this disclosure. These features are believed to be applicable in a wide variety of systems including one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a," "an," and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit (ASIC), and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program storage in memory for execution by personal computers, workstations, clients, and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Furthermore, as used herein, the term "real-time" refers to at least one of the time of occurrence of the associated events, the time of measurement and collection of predetermined data, the time for a computing device (e.g., a processor) to process the data, and the time of a system response to the events and the environment. In the embodiments described herein, these activities and events occur substantially instantaneously.

The present systems and methods herein advantageously implement technological protection mechanisms that prohibit prescription-seekers from fraudulently or accidentally abusing prescriptions (e.g., controlled substances, such as narcotics, etc.) using consensus-based databases. The protection mechanisms described herein are further useful for detecting fraud, abuse, or waste by physicians, medical facilities, pharmacies, and insurance providers/payors.

In some embodiments, the present systems and methods may be further configured to advantageously utilize distributed ledgers to confirm and/or record the status of consumable goods, for example, from prescription to fulfillment. The present embodiments may be implemented to augment or, in some circumstances, replace conventional tracking and security practices that rely on trusted parties to manually record events into databases or other record keeping mechanisms, such as trusted labels or tags, including bar codes, RFID tags, or other device identification methods. The distributed ledgers described and illustrated herein may include, for example, blockchain technology to create digital ledgers for tracking the status, location, and/or disposition of consumable goods. For ease of explanation, the following description references blockchains as an exemplary embodiment of distributed ledger technology. A person of ordinary skill in the art though, upon reading and comprehending the present description and associated illustrations, will understand that other examples of distributed ledger technologies may be implemented according to the novel and advantageous principles herein.

That is, in the following disclosure, the phrases "distributed ledger" and "blockchain" are used. In conventional practice literature, these two concepts are often considered to be synonymous. However, within this application, the two concepts may further differ in terms of their respective use and implementation. For example, in some instances the phrase "distributed ledger" may refer to how the ledger or blockchain is used, namely, the accessible distributed ledger as available to prove the facts of a transaction by virtue of being distributed amongst a consensus pool. A "blockchain," on the other hand, may refer to the process by which the distributed ledger is created and operated. Accordingly, a blockchain will create a distributed ledger, but a distributed ledger may be created by other technologies as well. In the following description, the phrase "digital ledger" is utilized to refer to either or both of the distributed ledger and the blockchain.

The present solutions are thus advantageously implemented as either standalone systems, or as complementary systems to conventional recording systems that rely on trusted parties manually recording events into databases or other record keeping mechanisms, often using trusted labels. In such systems, it is important to track and verify information (e.g., specific times, location, duration, quantity, status, etc.) of consumable goods move through/traverse a physical system or telecommunications network. The present embodiments are therefore of particular application to fields such as medical consumables (e.g., drugs and pharmaceuticals) that are at particularly high risk of abuse and/or fraud. In some embodiments, registration of the status of goods on the distributed ledger or blockchain may be implemented together with conventional identification and authentication processes, such as bar code scanning, RFID tagging, near field communications, biometrics, manual entries, etc.

According to the embodiments herein, digital ledgers are implemented to create secure and immutable records of transactions regarding the movement or status of consumable goods, or "consumables." In these records, the transaction information is encoded into formats, digitally signed using a cryptographic technique, and submitted to a network of processors of a distributed ledger network. The processors validate the submitted transactions for accuracy, and the validated transactions are subsequently added to a queue or stack of the ledger. At some point, according to a predetermined criterion (such as, but not limited to, an interval of time, a volume of data, a number of transactions, or combination of these and other factors), the queued or stacked transactions are sequentially hashed (e.g., using a Merkle process), and collectively encoded into a block which is then hashed with the hash of the proceeding block using cryptographic processes. An algorithm will allow multiple processors to select a block from amongst many processors to be the block added to the blockchain.

In an exemplary embodiment, the distributed ledger is a blockchain. Blockchaining technology takes transaction information, encapsulates it in a digital envelope or "block" and then the block is cryptographically added (using cipher chaining techniques) to the end of a chain of other transactions. This cryptographic addition incorporates information from prior blocks on the chain to calculate the digital chain or "hash" for this new block. The calculations for cryptographic addition can vary widely in complexity based on the rules of the blockchain. This complexity is purposeful though, in order to prevent modification of the existing blockchain to which is being added. That is, in order to modify an earlier block in the chain, the entire chain from that point forward would need to be recalculated. It is through this technique that the immutability of the chain, and permanency of its public ledger, is maintained. Exemplary systems and methods of blockchain technology are described in greater detail in co-pending U.S. patent application Ser. No. 15/345,411, filed Nov. 7, 2016, U.S. patent application Ser. No. 15/376,375, filed Dec. 12, 2016, U.S. patent application Ser. No. 15/476,111, filed Mar. 31, 2017, and U.S. patent application Ser. No. 15/476,098, filed Mar. 31, 2017, all of which are incorporated by reference herein.

In the following embodiments, digital ledgers are utilized and/or created to track the status and movement of consumable goods. In an exemplary embodiment, the digital ledger is implemented to register relevant IDs of one or more of a physician and a consumer/patient ID, and then reliably track the status of a prescribed pharmaceutical from the time of the prescription by the physician until the time of fulfillment or distribution to the consumer/patient. According to the advantageous systems and methods described herein, the digital ledger may be utilized to automatically supplement, or substitute for, conventional practices that rely on trusted parties to manually record events into databases or other electronic record keeping mechanisms. In some embodiments, the present systems and methods utilize their own unique device technology to identify a person for association with one or more devices. In other embodiments, the present systems and methods may be implemented utilizing existing trusted identification technology, such as barcodes, RFID tags, biometric identifiers, etc.

The exemplary embodiments are described herein with respect to an ecosystem for securely tracking consumable pharmaceutical goods. A person of ordinary skill in the art though, will understand that the present systems and methods are applicable, in whole or in part, with respect to other types of consumable goods, and particularly goods of high value (e.g., legal tender, etc.). In an exemplary embodiment, an ecosystem implements a distributed ledger to better enable secure, attestable, and validated prescription pharmaceutical transactions. According to the innovative techniques provided herein, prescription abuse, misuse, and error are significantly reduced.

In an embodiment, a distributed ledger ecosystem supports visibility and validation of prescriptions for multiple hospitals, physicians, and/or care offices, to provide improved distribution and dispensation of high value/high risk consumable goods (e.g., pharmaceutical drugs). The present embodiments enable the ecosystem to more reliably prevent use of the same pharmaceutical prescription for multiple fulfillments. An ecosystem according to the present embodiments further enables a prescriber or prescribing office to more visibly verify that a prescription has been fulfilled.

The present systems and methods are of particular useful advantage to law enforcement, pharmacies, medical institutions, health insurance providers/payors, and prescribing physicians. Additionally, communication network operators are able to provide an improved infrastructure for institutions, campuses, and satellite offices (e.g., medical care, pharmaceuticals, etc.), thereby also providing a significantly stronger and more secure vector for differentiation among use cases.

The embodiments described herein are further useful for reliably associating an individual pharmaceutical prescription with a particular person, and within a particular period of time. As described herein, details of transaction events (e.g., current status, changes in status, pre-fulfillment, post-fulfillment, etc.) for a particular consumable good/medication. The transactions may be encoded into a cryptographically signed and protected transaction that is submitted to a distributed ledger network, such as a blockchain network, for further processing. Processors of the distributed network process the incoming transactions into blocks, which may then be added to a particular blockchain. Once added to the blockchain (or equivalent entry in an electronic distributed ledger), the transaction is visible to, but immutable by, appropriate parties that seek to create a history of disposition and movement of the goods. Such histories may then be more easily verified on the ledger, while being rendered more difficult to alter once added to the ledger. In some embodiments, the ledgers further track the association of persons to the prescriptions, goods, and transactions of the ecosystem.

In the exemplary pharmaceutical embodiment illustrated herein, patients, physicians, pharmacies, medical care facilities, and payor interact within an ecosystem using one or more registries and a distributed ledger to memorialize each interaction or transaction. In this example, each party in the ecosystem has its own unique identity/identifier used throughout the ecosystem, to which may be assigned respective public/private keypairs of a public key infrastructure (PKI). The participants then interact through transactions which are recorded on a shared registry (i.e., distributed ledger, blockchain, etc.).

FIG. 1 is a schematic illustration of an ecosystem 100 for fulfillment of a consumable good order by a consumer. In an exemplary embodiment illustrated in FIG. 1, the consumer is a medical patient, the consumable good is a pharmaceutical drug, and the order is a medical prescription for the drug. This example is provided by way of illustration though, and should not be considered limiting. The principles of the present embodiments may be applied to other types of consumers, goods, and orders.

In the exemplary embodiment, ecosystem 100 includes a patient ID 102 of the consumer. Patient ID 102 may include, for example, identifying information of the consumer, including without limitation one or more of a name/full name, address, Social Security number, a driver's license picture, and biometric data, such as a fingerprint, iris scan, physical signature, etc., which may be assigned or matched with a cryptographic identifier. Ecosystem 100 further includes a medical computer system 104, a fulfillment computer system 106, a payor computer system 108, an ID registry 110, a transaction registry 112, and a distributed ledger 114. Optionally, ecosystem 100 further includes a monitoring computer system 116. In some embodiments, monitoring computer system 116 is associated with one of the respective participant systems 104, 106, 108 of ecosystem 100. In other embodiments, monitoring computer system 116 is an independent portion of ecosystem 100.

In some embodiments, ID registry 110 and transaction registry 112 are maintained together as part of the same database. In other embodiments, ID registry 110 is securely maintained separate and apart from transaction registry 112, and no information is shared therebetween (e.g., such as in the case of strict medical information privacy rules and regulations governing access to medical information contained within ID registry 110).

Ecosystem 100 is illustrated to depict an exemplary architecture for implementing the distributed ledger embodiments of the present disclosure. Other architectures though, are contemplated by the present inventors, which do not depart from the scope of the embodiments described herein. Furthermore, for ease of explanation, redundant components that may be implemented within system 100 are not illustrated, nor are link-level objects or implementations, security authentication objects, sequences, and implementations, nor other components that may be conventionally utilized in a distributed ledger network for communication, availability, or security purposes. In an exemplary embodiment of system 100, transaction events are communicated by nodes (not shown) respectively associated with one or more of the ecosystem participants, in such nodes are configured to communicate with processors (also not shown) of distributed ledger 114.

Medical computer system 104 (hereinafter, physician 104) may represent an electronic device, interface, computer, or computer network of a physician or medical care facility that is capable of electronically accessing (e.g., over the Internet, LAN, WAN, WLAN, etc.) ecosystem 100 and distributed ledger 114, and signing transactions with a cryptographic ID assigned to physician 104 (or a person represented by/as physician 104, such as a prescribing physician). Similarly, fulfillment computer system 106 (hereinafter, pharmacy 106) may represent a secure electronic device or computer system of the pharmacy or pharmaceutical distribution repository, and payor computer system 108 (hereinafter, payor 108) may represent a secure electronic device or computer system of a medical insurance payor, both of which are capable of signing electronic transactions with their own cryptographic signatures.

In the exemplary embodiment, relationships between participants of ecosystem 100 may be established in advance, or according to one or more of the several processes described herein. From these relationships, some level of access to a prescription registry (e.g., ID registry 110) is allowed for each participant. Where the consumer is, for example, a medical patient, the patient requests or receives prescriptions for a pharmaceutical good from a physician or medical care facility (e.g., physician 104), who in turn submits transactions to the shared ledger (e.g., distributed ledger 114). Individual transactions may then be assigned their own unique transaction IDs to enable further use. The patient (e.g., using patient ID 102) requests fulfillment of the prescription from pharmacy 106. Pharmacy 106 validates patient ID 102 (e.g., with ID registry 110) and generates at least one transaction ID to send to transaction registry 112. Ecosystem transactions that are verified as being both valid are fulfilled, that is, "spent," are submitted to distributed ledger 114 for secure recording thereof. Recording of a spent transaction on distributed ledger 114 will advantageously prevent a prescription from subsequently being fulfilled by another, or the same, pharmacy 106.

An exemplary operation of ecosystem 100 is described in greater detail below with respect to FIGS. 1-3. In the exemplary embodiment illustrated in FIG. 1, ecosystem 100 is illustrated with respect to a registration process 118. Process 118 may, for example, represent an a priori registration process performed between a patient and an insurance company prior to a specific prescription order and subsequent development (e.g., when a patient establishes a health insurance account with payor 108). Alternatively, process 118 may be implemented as an initial subprocess when a patient (e.g., using patient ID 102) seeks fulfillment of a prescription order from pharmacy 106. In the case where the patient does not have medical insurance, process 118 may be skipped, and fulfillment of the prescription order may begin at process 200, FIG. 2, below.

In the exemplary embodiment, process 118 begins at step S120, in which the patient establishes a relationship with payor 108 (e.g., requests insurance coverage or registration of a prescription card account). In an exemplary embodiment of step S120, the patient establishes the relationship using patient ID 102. In other embodiments, patient ID 102 is generated by payor 108 in response to a registration request from the patient. In step S122, payor 108 stores patient ID 102 in ID registry 110. In step S124, ID registry 110 associates patient ID with at least one payor ID (e.g., insurance group or plan a number, etc.) stored within ID registry 110, and records the association on distributed ledger 114. In step S126, the payor 108 establishes a fulfillment account and/or issues a "patient ID card" to the patient/consumer. This patient account/ID card memorializes the relationship between the patient and payor 108, which may then be used in subsequent fulfillment transactions.

In an optional embodiment, ecosystem 100 is also configured to enable physician 104 to establish a unique relationship with ID registry 110 as well. For example, in step S128, physician 104 transmits a registration request to ID registry 110. In an exemplary embodiment of step S128, physician 104 submits at least one state license number of a physician to ID registry 110, as well as other physician/facility identifying information that may be requested by ID registry 110. In step S130, ID registry 110 verifies that the state license submitted by physician 104 is in good standing, assigns a unique cryptographic key (i.e., different from a physician state ID) for physician 104 to use in subsequent transactions with ecosystem 100, and records the assignment with distributed ledger 114.

In an exemplary embodiment of step S130, verification of information submitted by physician 104 is repeated periodically. In other embodiments of step S130, verification occurs after expiration of a predetermined time period, or in response to a specific event (e.g., notification of disciplinary action against a physician). One or both of steps S128 and S130 may be performed before, during, or after steps S120 through steps S126, and physician registration ecosystem 100 may be performed independently of patient registration.

In the exemplary embodiment illustrated in FIG. 1, transaction steps are described relative to how a respective transaction is submitted to, and recorded on, distributed ledger 114. Individual process steps that may also be performed by ecosystem participants (or persons and/or devices associated therewith) are not illustrated, for ease of explanation. That is, ecosystem 100 is described herein primarily with respect to its ability to interact with distributed ledger 114, and is not intended to describe all other potential processing steps for initiating, validating, and appending transactions to distributed ledger 114 that may be performed by persons (e.g., including manual entries) or other devices (e.g., data transmissions, communication protocols, etc.), as described above with respect to the co-pending patent applications incorporated by reference.

In some embodiments, distributed ledger 114 utilizes a certificate authority (not shown) as a trusted entity in order to validate digital signatures against electronic documents and/or digital certificates issued by the certificate authority to verify the identity of one or more of the ecosystem participants for each transaction. Such digital certificates may, for example, be implemented according to secure communication techniques such as PKI. In the exemplary embodiment, each of the ecosystem participants is enabled to directly or indirectly use electronic communication means for wired or wireless electronic communication over an electronic network.

As described above, the exemplary embodiments of ecosystem 100 are described with respect to medical consumables, such as controlled substances. Nevertheless, a person of ordinary skill in the art will understand, upon reading and comprehending the present application, how the principles of ecosystem 100 apply to other fields (e.g., law enforcement, smart contracts, etc.) where secure and transparent tracking (physical or virtual movement) of a consumable is desirable and/or valuable. Accordingly, distributed ledger 114 may include a blockchain network, or a blockchain, and ecosystem 100 may advantageously leverage digital signatures/hashes and/or Merkle roots/trees to reliably monitor and track the consumable status and movement using the blockchain.

In some embodiments of ecosystem 100, some or all of the ecosystem participants are in direct or indirect operable communication with an electronic communications network (e.g., Internet, LAN, WAN, WLAN, etc.). In at least one embodiment, one or more of the participants is further in operable communication with a certificate authority (not shown), such as in the case where access to, or verification of, digital certificates is desired. That is, a certificate authority may be utilized to verify the digital identities of the respective participants on the electronic communications network and issue a digital certificate to function as a trusted root certificate (e.g., embedded in hardware or software of the one or more participants) for the respective transactions. In an exemplary embodiment, distributed ledger 114 is a blockchain, and PKI-based certificates are utilized to implement secure communication between, and authentication of, the ecosystem participants for each transaction.

In exemplary operation, each transaction is submitted to distributed ledger 114, verified by the processors thereof (e.g., by a consensus model), and then recorded as new blocks onto the ledger. In this example, each of the participants includes or is assigned a party-specific ID that may be digitally verified by the blockchain for each respective transaction. Patient ID 102, for example, may include a wearable coded wristband if the patient in a hospital, or alternatively, may represent a physical ID (e.g., a driver's license) that is capable of being scanned or recorded by pharmacy 106 and then digitally verified by distributed ledger 114.

Figure 2:
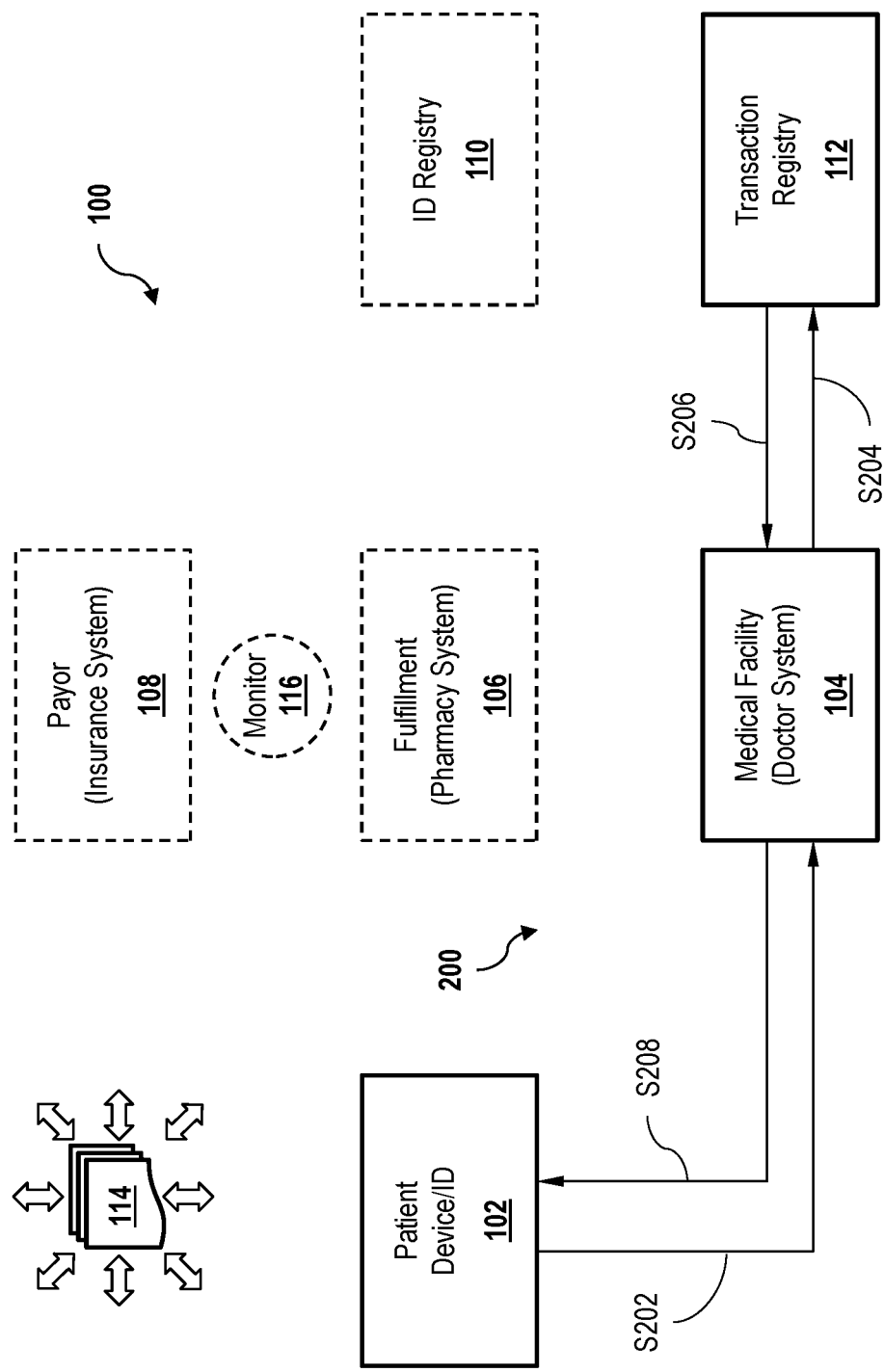
FIG. 2 is a schematic illustration of a prescribing process for the ecosystem depicted in FIG. 1.

FIG. 2 is a schematic illustration of a prescribing process 200 for ecosystem 100, FIG. 1. In an exemplary embodiment, process 200 is implemented in a complementary fashion with process 118, FIG. 1, namely, after registration of one or both of a patient and a prescribing physician. In other embodiments, process 200 may be implemented independently of process 118, or process 118 may be implemented in whole or in part, during or after completion of process 118.

Process 200 begins at step S202, in which a patient contacts a physician/medical facility of physician 104 for medical services. In an exemplary embodiment of step S202, the medical services for the patient include a request for a prescription refill of a controlled substance, or results in a determination by a physician that the patient requires a prescription for a controlled substance. In step S204, a prescription order is issued by physician 104 to transaction registry 112. In an exemplary embodiment of step S204, issuance of the prescription order includes one or more of patient ID 102 (e.g., obtained from ID registry 110), personal identification information of the patient that can be matched with patient ID 102, and the unique physician key or cryptographic ID assigned for use within ecosystem 100 (e.g., from step S130, FIG. 1). In at least one embodiment of step S204, physician 104 may perform the steps S128 and S130 at this time (e.g., if not completed earlier).

It should be noted that, in the case where a prescription pad is stolen from a licensed physician, the stolen prescription pad itself would not include the unique physician ID, which is different from the physician state licensing number (which sometimes is printed on prescription pads). By assigning a separate unique ID for the position within ecosystem 100, an additional level of security is provided against such types of theft.

In step S206, transaction registry 112 generates a unique transaction ID for the subject prescription order, which is then registered on distributed ledger 114. In an exemplary embodiment of step S206, transaction registry 112 is further configured to verify, before generating the transaction ID, that the prescription order is not a repeat prescription, or a second prescription of the same pharmaceutical good within a predetermined time period. In step S208, physician 104 generates a prescription order for the patient using the transaction ID received from transaction registry 112, and the prescription order is also registered with distributed ledger 114 (e.g., as its own unique transaction, or as information appended to the same prescription transaction).

In some embodiments, the generation of the prescription order is performed electronically, and submitted directly to pharmacy 106, including the unique IDs associated with the prescription order (transaction ID, physician ID, patient ID 102, etc.). In other embodiments, the transaction ID is associated with the prescription order, and the patient receives a written prescription order document that may be physically taken to a distribution location of pharmacy 106. As explained further below with respect to FIG. 3, in such instances, ecosystem 100 enables pharmacy 106 to look up the prescription order on the document with transaction registry 112, match the prescription order to the transaction ID generated by transaction registry 112, and verify that the transaction thereof (i.e., the prescription order) is not "spent." In at least one embodiment, where physician 104 might not be registered within ecosystem 102 have a unique physician ID, the transaction ID may be alternatively generated in response to a fulfillment request from pharmacy 106, after verifying (e.g., with distributed ledger 114) that there is no pending or spent transaction/transaction ID associated with the specific prescription order.

Figure 3:
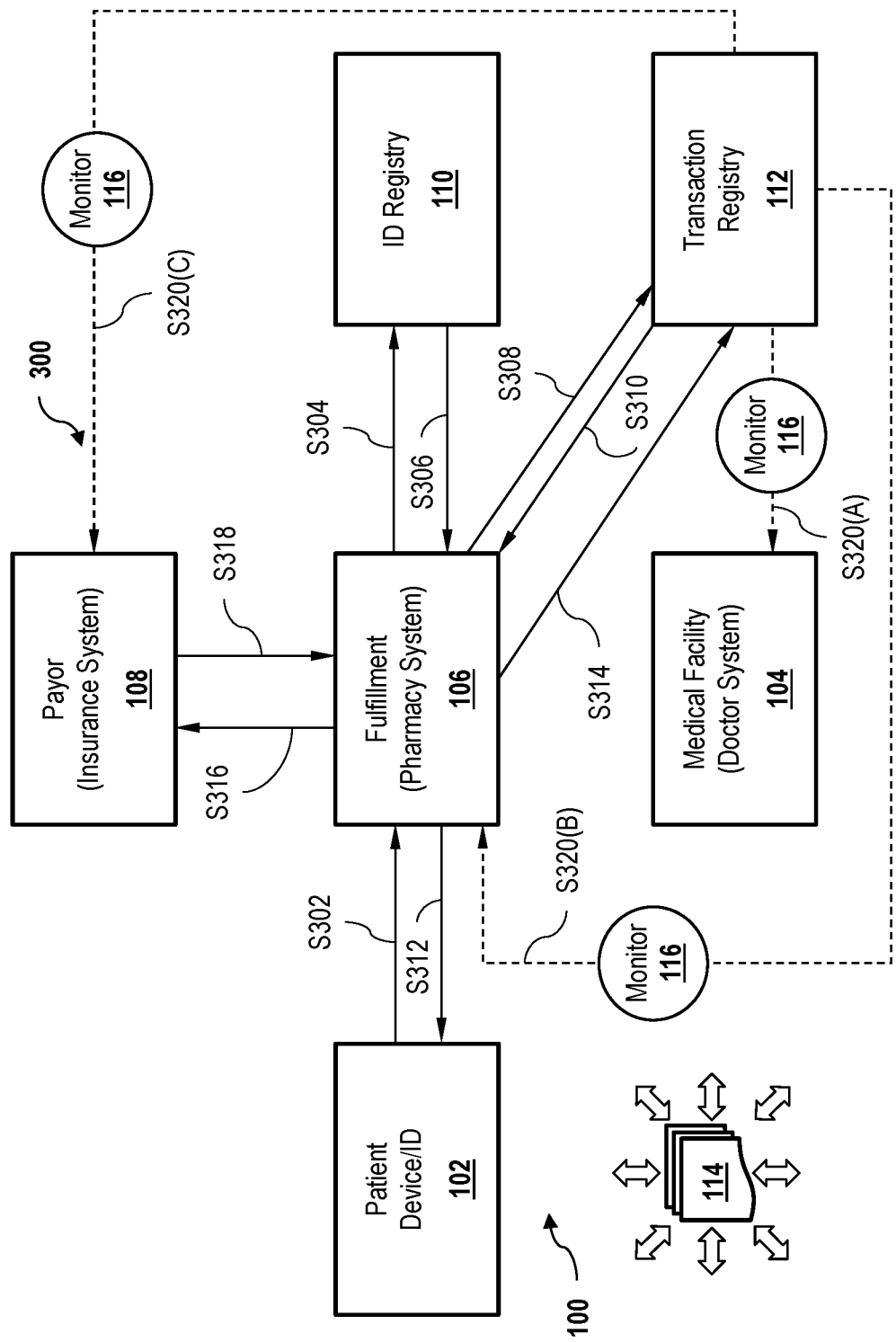
FIG. 3 is a schematic illustration of a fulfillment process for the ecosystem depicted in FIG. 1.

FIG. 3 is a schematic illustration of a fulfillment process 300 for ecosystem 100, FIG. 1. In an exemplary embodiment, process 300 is implemented in a complementary fashion with one or both of process 118, FIG. 1, in process 200, FIG. 2, or respective portions thereof. In some embodiments, process 300 may be implemented independently of all or some portions of processes 118, 200. Except where otherwise stated to the contrary, the several steps of the various processes 118, 200, 300, may be performed in a different order, interspersed, in sequence, and/or simultaneously.

Fulfillment process 300 begins at step S302, in which the patient seeks fulfillment of a prescription order from pharmacy 106. In an exemplary embodiment of step S302, the prescription order is submitted to pharmacy 106 using patient ID 102 and a unique transaction ID generated for the prescription order (e.g., from step S206). In step S304, pharmacy 106 submits patient ID 102 to ID registry 110 for verification. In an exemplary embodiment of step S304, verification of patient ID 102 includes matching of one or more pieces of personal identification information (e.g., driver's license, etc.) from the patient with information stored in ID registry 110 and associated with patient ID 102 therein. In step S306, ID registry 110 verifies patient ID 102 (e.g., by querying distributed ledger 114) and notifies pharmacy 106 of the verification. In at least one embodiment of step S306, process 300 may additionally verify the unique ecosystem ID of physician 104.

In step S308, pharmacy 106 submits the transaction ID to transaction registry 112 for validation. In step S310, transaction registry 112 validates (e.g., including a query to distributed ledger 114) that the prescription order is legitimate and not spent, and notifies pharmacy 106 of the validation. Step S308 may, for example, be performed simultaneously with step S304, or in a different order therewith. In the exemplary embodiment though, both of steps S306 and S310 should be completed prior to proceeding to step S312.

In step S312, pharmacy 106 fulfills the prescription order (e.g., physically provides a quantity of a controlled substance to the patient), and the fulfillment is recorded on distributed ledger 114. In step S314, pharmacy 106 additionally updates transaction registry 112 of the fulfilled prescription order. This update to transaction registry 112 advantageously enables ecosystem 102 prevent the prescription order from being filled twice, that is, by the same or a different pharmacy 106, whether through inadvertent error or by intentional misuse. In either case, ecosystem 100 enables a patient, physician, pharmacy, payor, or law enforcement personnel to query distributed ledger 114 and verify specific details of the transaction (e.g., who, what, when, where, etc.).

In some embodiments, process 300 additionally performs step S316, in which pharmacy 106 contacts payor 108 to verify insurance/payment coverage of the purchase of the pharmaceutical good of the particular transaction. In step S318, payor 108 notifies pharmacy 106 of the relevant coverage, if any. In an exemplary embodiment of step S318, payor 108 further notifies pharmacy 106 of how much time has elapsed since a previous transaction for the same pharmaceutical good by the same patient, and/or how much time remains before a subsequent refill is authorized. Steps S316 and S318 may be performed any time after execution of step S302, and in any particular order with respect to the other steps described above, independently or in a complementary fashion.

In an optional embodiment, ecosystem 100 is further configured to provide observation capability through implementation of monitoring system 116. That is, in at least one embodiment, monitoring system 116 is configured to proactively monitor, in step S320, the various transactions recorded between transaction registry 112 and, for example, physician 104 (i.e., step S320(A)), pharmacy 106 (i.e., step S320(B)), or payor 108 (i.e., step S320(C)). This additional observation capability advantageously enables ecosystem 102 more proactively detect fraud and abuse, such as in the case of stolen prescriptions or prescription pads, and affirmatively notify (e.g., by an automatic alert) the appropriate participants. This additional capability is useful in the case where a fulfillment provider loses the hard copies (or duplicates) of written prescriptions. In the case of a stolen prescription pad, for example, a prescription order written therefrom will not associate with a transaction ID in transaction registry 112. In this case, monitoring system 116 may be configured to automatically flag any such prescription written from this likely stolen prescription pad.

The present embodiments also particularly useful in the case of monthly, or automatic, refills of a prescription for patient. In such instances, ecosystem 100 may be further configured such that transaction registry 112 generates a new unique transaction ID for each authorized refill, which may then be individually fulfilled according to the systems and methods described above. This advantageous configuration provides greater flexibility and ability to patients and physicians, different pharmacies may be more easily contacted to fulfill recurring prescription orders. The different pharmacies need only query the transaction registry (e.g., in cooperation with distributed ledger 114) to verify that the particular refill transaction has not been spent. Conventional systems require a cumbersome process approval and transfer of patient information between pharmacies before separate refill occurrences may be fulfilled among different pharmacies.

The present embodiments are also advantageous in the case of a particular prescription order being only partially fulfilled, that is, not completely fulfilled according to the particular prescription order corresponding generated transaction ID. In this case, each partial fill of the original prescription transaction may generate its own transaction ID (e.g., separately encoded with the relevant details particular to both that prescription transaction and the original prescription transaction, including the patient ID, quantity, etc.), associated with the original transaction ID within the transaction registry, and submitted to the distributed ledger for validation and entry based on the original transaction ID (e.g., including the genesis transaction block and initial entry transaction block of a blockchain). According to this innovative technique, a patient may refill various portions of a single prescription at several pharmacies without having to go through the cumbersome process of transferring the entire prescription from one pharmacy to another.

In some embodiments, the present systems and methods may be further implemented with respect to smart contracts, which may advantageously provide conditional execution of the various transactions performed within the ecosystem, and which also enable logical and mathematical processes related to the prescription and fulfillment details (e.g., "refillable X number of times," maximum number of doses, etc.). The present embodiments may further include additional monitoring/observation capability that we notify, for example, physicians when prescriptions have been fulfilled, payors of a new prescription, or patients when a prescription is due for a refill. The present embodiments still further provide more reliable means of authentication of transactions by physicians and/or pharmacies who have relationships with individual patients contracting with the payor. Some or all of these additional implementations may be performed independently, or in a complementary fashion using the distributed ledger.

As described above, the embodiments herein implement distributed ledger technology, and are not limited solely to blockchains. A blockchain is theoretically perpetual, however, at a fundamental level, the notion that a particular blockchain is eternally viable (or even viable for many decades or longer) may not be a reasonable assumption, even as technology continues to improve. Furthermore, it is an unlikely expectation that all transactions within a blockchain will be able to stand on a queue or list indefinitely. Accordingly, it is contemplated herein that the systems and methods the present embodiments may further implement recovery and/or damage containment mechanisms to mitigate the effects of corruption of a monolithic blockchain or of a blockchain forest.

In some of the embodiments described above, a blockchain may implement a registration model, to advantageously achieve centralization, and to provide further stability and predictability to a blockchain ecosystem. Alternatively, a blockchain may implement a consensus model to provide additional security to the blockchain ecosystem. In the consensus model alternative, for example, particular participant roles within the distributed ledger network may be integrated in multiple processors capable of negotiating participation and fulfillment operations collectively, utilizing either another blockchain (e.g., a management blockchain), or a consensus driven database (such as Cassandra).

In some embodiments, the security of new blockchains may be improved by including a blockchain hash from another chain, either from within a blockchain forest, or from an independent blockchain (such as Bitcoin). This separate hash may be included as part of the archival process, or may be included prior to archival from within the lifecycle of the blockchain. Accordingly, milestones of one blockchain may then be communicated and distributed to other blockchains as transactions. These new transactions can be performed at defined time intervals, at defined block heights (e.g., as part of instantiation and/or user request requirements), or associated with other activity within a blockchain forest (e.g., when another blockchain is instantiated or destroyed). An additional blockchain forest mechanism may serve to advantageously create a lattice of blockchains that is more secure than conventional monolithic implementations because adversaries of the blockchain are now required to attack multiple blockchains to perform a history attack, for example. The present embodiments may further be capable of terminating corrupted blockchains that are no longer useful, and thereby improve the security of blockchains having a smaller number of participants.

Irrespective of the particular architecture/methodology of the blockchain/distributed ledger, the present systems and methods realize still further advantages over conventional consumable tracking systems and techniques. For example, where federal regulations prevent unused controlled substances from being recycled, redistributed, or otherwise reused, a black market sometimes exists for selling such controlled substances that should have been destroyed. Through the advantageous techniques of the present embodiments, disposition of the status of a particular consumable is easier to transparently and verifiably monitor, and appropriate parties may be given a timely alert upon the unauthorized transfer (e.g., theft) of a controlled substance or prescription order therefor, or an attempt to redistribute a controlled substance that is intended for destruction.

The innovative embodiments described herein may also utilize hyper ledgers, which represent a cross-industry collaboration to develop blockchains and/or distributed ledgers having improved performance and reliability capable of supporting global business transactions by major technological, financial, and supply chain companies. Hyperledgers integrate independent open protocols and standards through a framework of use-specific modules, including blockchains having their own consensus and storage routines, in addition to service modules for identity, access control, and smart contracts.

The systems and methods described herein therefore allow for the ability to more securely encode the consumptions of materials, and track and execute the encoded transactions in immutable distributed ledgers that are more reliable than conventional systems, while also providing greater transparency. The details of the consumables and related transactions may be asserted through secure off-chain interfaces, or alternatively may be encoded directly into each transaction submitted to the digital ledger. The present systems and methods, by cryptographically protecting transactions and recording the cryptographically protected transactions on the distributed ledger, may operate as a stand-alone system, or may advantageously complement conventional material management processes and tracking techniques. Different from conventional systems, the present embodiments may be used to assure that persons responsible for physical material management steps or virtual data entry are trusted parties that physically or virtually execute the relevant associations, deliveries, and other status changes of the tracking system. Each such trusted party may therefore have its own secure ID (e.g., public and private keys, or equivalent token mechanism) which is included in each relevant transaction that results in a change of status of the respective consumable goods.

Exemplary embodiments of spectrum sharing management systems and methods are described above in detail, and more particularly, embodiments relating to beacon detection system configuration and operation. The systems and methods of this disclosure though, are not limited to only the specific embodiments described herein, but rather, the components and/or steps of their implementation may be utilized independently and separately from other components and/or steps described herein.

Although specific features of various embodiments may be shown in some drawings and not in others, this is for convenience only. In accordance with the principles of the systems and methods described herein, any feature of a drawing may be referenced or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a programmable logic unit (PLU), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ecosystem for monitoring a status of a fulfillment order for a consumable good, comprising:
a distributed ledger network comprising a plurality of communication nodes in operable communication with at least one ledger processor,
the distributed ledger network implementing a distributed ledger;
an identification registry including at least one identification registry processor and at least a first non-transitory computer readable medium comprising a first electronic database and executable instructions, that, when executed by the at least one identification registry processor cause the identification registry to:
(i) store, within the first electronic database, identifying digital identification information regarding a consumer, and
(ii) associate, within the identification registry, the stored identifying digital identification information with a first unique cryptographic identifier for the consumer;
a transaction registry including at least one transaction registry processor and at least a second non-transitory computer readable medium comprising a second electronic database and executable instructions, that, when executed by the at least one transaction registry processor, cause the transaction registry to:
(i) receive digital order information from a remote prescriber computer subsystem, the digital order information representing a fulfillment order request for a fulfillment order, the digital order information comprising a quantity of the consumable good, one or more of the digital identification information and the first unique cryptographic identifier,
(ii) generate, within the transaction registry, a second unique cryptographic identifier associated with the digital order information,
(iii) further generate, within the transaction registry, a fulfillment status of the fulfillment order request, and
(iv) submit the second unique cryptographic identifier to the distributed ledger for encoding as an initial entry transaction block on the distributed ledger; and
a fulfillment computer subsystem including at least one fulfillment computer processor and at least a third non-transitory computer readable medium comprising instructions that, when executed by the at least one fulfillment computer processor, cause the fulfillment computer subsystem to:
(i) receive the first unique cryptographic identifier and the fulfillment order, wherein the fulfillment order includes the digital order information and the second unique cryptographic identifier,
(ii) verify, after receipt of the first unique cryptographic identifier and the fulfillment order, the first unique cryptographic identifier with the distributed ledger,
(iii) validate, after receipt of the fulfillment order, the second unique cryptographic identifier with the distributed ledger,
(iv) query the transaction registry as to the fulfillment status of the fulfillment order,
(v) receive, after querying the transaction registry, a notification that the quantity of the consumable good has been distributed to the consumer, and
(vi) update the transaction registry, after receipt of the notification, and using the second unique cryptographic identifier, to record the fulfillment status of the fulfillment order as spent;
wherein the transaction registry and the fulfillment computer subsystem interact with the distributed ledger through at least one of the at least one ledger processor and at least one of the plurality of communication nodes.

2. The ecosystem of claim 1, wherein the distributed ledger network comprises a blockchain.

3. The ecosystem of claim 2, wherein the blockchain includes a genesis transaction comprising a cryptographic digital signature corresponding to the initial entry transaction block.

4. The ecosystem of claim 2, wherein the blockchain is configured to execute a transaction validation using one of a consensus model and a registration model.

5. The ecosystem of claim 1, wherein the distributed ledger is further configured to validate one or more transaction blocks using a public key infrastructure.

6. The ecosystem of claim 1, wherein transaction details are encoded into the distributed ledger by one of (i) direct encoding, and (ii) assertion through a secure off-chain interface device in communication with at least one of the at least one ledger processor and the one or more communication nodes.

7. The ecosystem of claim 1, further comprising a monitoring subsystem including at least one monitoring processor and at least a fourth non-transitory computer readable medium comprising executable instructions, that, when executed by the at least one monitoring processor cause the monitoring subsystem to: observe one or more ecosystem transactions between the transaction registry and at least one of (i) the fulfillment computer subsystem, and (ii) the prescriber computer subsystem.

8. The ecosystem of claim 7, wherein the at least fourth non-transitory computer readable medium further comprises executable instructions, that, when executed by the at least one monitoring processor cause the monitoring subsystem to: observe a particular transaction and transmit a notification, upon observation of the particular transaction, indicating that (i) the first unique cryptographic identifier of the consumer is not verified by the identification registry, or (ii) the second unique cryptographic identifier is not validated by the transaction registry.

9. The ecosystem of claim 1, wherein the fulfillment computer subsystem is associated with a pharmacy, the consumable good is a pharmaceutical material, and the fulfillment order comprises a medical prescription order.

10. The ecosystem of claim 9, wherein the at least third non-transitory computer readable medium of the fulfillment computer subsystem further comprises instructions that, when executed by the at least one fulfillment computer processor, cause the fulfillment computer subsystem to: authorize the distribution of the quantity of the pharmaceutical material to the consumer upon (i) verification of the first unique cryptographic identifier by the identification registry, and (ii) validation of the second unique cryptographic identifier by the transaction registry.

11. The ecosystem of claim 10, wherein the at least third non-transitory computer readable medium of the fulfillment computer subsystem further comprises instructions that, when executed by the at least one fulfillment computer processor, cause the fulfillment computer subsystem to: notify the transaction registry to record, in the second database of the transaction registry, a successful fulfillment of the medical prescription order.

12. The ecosystem of claim 11, wherein the at least second non-transitory computer readable medium of the transaction registry further comprises instructions that, when executed by the at least one transaction registry processor, cause the transaction registry to: submit, to the distributed ledger, the fulfilled medical prescription order for encoding as a spent transaction block encoded on the distributed ledger subsequent to the encoding of the initial entry transaction block.

13. The ecosystem of claim 1, wherein the distributed ledger network is further configured to validate encoded transaction information using a certificate authority of a trusted entity.

14. The ecosystem of claim 13, wherein the distributed ledger network is further configured to validate digital signatures of one or more ecosystem transactions submitted to the distributed ledger against digital certificates issued by the certificate authority.

15. The ecosystem of claim 14, wherein the digital certificates issued by the certificate authority implement a public key infrastructure.

16. The ecosystem of claim 13, wherein the certificate authority is in operable communication with one or more of the prescriber computer subsystem, the fulfillment computer subsystem, the at least one of the at least one ledger processor and the one or more communication nodes, the identification registry, the transaction registry, and an electronic device of the consumer.

17. The ecosystem of claim 1, wherein the identification registry is in operable communication with at least one of the prescriber computer subsystem, the fulfillment computer subsystem, the at least one of the at least one ledger processor and the one or more communication nodes, and one or both of an electronic device of the consumer and a payor computer subsystem associated with the consumer.

18. The ecosystem of claim 8, wherein the transaction registry is in operable communication with at least one of the prescriber computer subsystem, the fulfillment computer subsystem, the at least one of the at least one ledger processor and the one or more communication nodes, and the monitoring subsystem.

19. The ecosystem of claim 1, wherein the identification registry and the transaction registry are located remotely from each other, and without direct communication capabilities therebetween.

20. The ecosystem of claim 1, wherein (a) the digital order information further comprises a government prescribing identifier stored in the identification registry, the government prescribing identifier configured to authorize at least one professional associated the prescribing computer system to issue the digital order information representing the fulfillment order for the quantity of the consumable good, and (b) the transaction registry is further configured to (i) match the received digital identification information of the consumer with the first unique cryptographic identifier, and (ii) authenticate a third unique cryptographic identifier associated with one or more of the at least one professional and the prescriber computer subsystem.

* * * * *